United States Patent

Starkey et al.

[11] Patent Number: 5,254,094
[45] Date of Patent: Oct. 19, 1993

[54] PHYSIOLOGICAL FLUID WARMER

[76] Inventors: David L. Starkey, 8724 Normandy La., Centerville, Ohio 45458; Feraidoon Irani, 8421 Schoolgate Dr., Huber Heights, Ohio 45424

[21] Appl. No.: 568,453

[22] Filed: Aug. 16, 1990

Related U.S. Application Data

[63] Continuation-in-part of Ser. No. 380,939, Jul. 17, 1989, abandoned.

[51] Int. Cl.⁵ .............................................. A61M 5/00
[52] U.S. Cl. ..................... 604/113; 607/104
[58] Field of Search ............... 604/113, 114; 128/399, 128/400, DIG. 3; 422/46; 165/67, 46, 156, 163

[56] References Cited

U.S. PATENT DOCUMENTS

| | | | |
|---|---|---|---|
| 3,612,059 | 10/1971 | Ersek | 128/399 |
| 3,881,483 | 5/1975 | Sausse | 128/214 |
| 4,047,563 | 10/1977 | Kurata | 128/400 |
| 4,158,693 | 6/1979 | Reed et al. | 128/DIG. 3 |
| 4,177,816 | 12/1979 | Torgeson | 128/400 |
| 4,293,762 | 10/1981 | Ogawa | 219/302 |
| 4,531,941 | 7/1985 | Zasuwa | 604/113 |
| 4,623,333 | 11/1986 | Fried | 604/80 |
| 4,705,505 | 11/1987 | Fried | 604/80 |
| 4,759,749 | 7/1988 | Verkaart | 604/113 |
| 4,787,833 | 11/1988 | Kroyer | 604/113 |
| 4,846,177 | 7/1989 | Leonard | 604/113 |
| 4,878,537 | 11/1989 | Verkaart | 604/113 |

FOREIGN PATENT DOCUMENTS 0256653 2/1988 European Pat. Off. ............ 128/399

OTHER PUBLICATIONS

Ahuja et al., Phys. Med. Biol., Sep. 1978, vol. 23, No. 5 pp. 937-951.

*Primary Examiner*—John D. Yasko
*Assistant Examiner*—Anthony Gutowski
*Attorney, Agent, or Firm*—Biebel & French

[57] ABSTRACT

A disposable physiological fluid warmer formed as a small compact box which may be attached to a patient's arm. The warmer includes two chambers within the box containing a heat exchanger element constructed from a continuous length of stainless steel tubing in the form of two parallel coils which are connected to one another by a straight length of tubing. A passage is provided along one side of the box between the chambers such that a warming fluid may be introduced through an aperture in the box into one of the chambers, flow into the other chamber, and then exit the warmer through another aperture in the box. A physiological fluid to be warmed is supplied to the coils through a first flexible plastic inlet tube and discharged for infusion into a patient through a second flexible plastic tube. The second tube has a length of less than one foot in order to minimize the amount of heat lost from the fluid as it travels from the warmer to the patient.

37 Claims, 5 Drawing Sheets

PHYSIOLOGICAL FLUID WARMER

CROSS-REFERENCE TO RELATED APPLICATION

This application is a continuation-in-part of coowned application Serial No. 380,939, filed Jul. 17, 1989 abandoned.

BACKGROUND OF THE INVENTION

The present invention relates to devices for warming physiological fluids and more particularly this invention provides a device for warming physiological fluids at a location which is closely adjacent to the point at which the fluid enters a patient.

Many physiological fluids, such as whole blood, packed red blood cells, and fresh frozen plasma are stored at cold temperatures as low as 4° C. until they are needed for a transfusion. While these fluids may be administered cold in small volumes or at low flow rates, for example, quantities of less than four 500 cc units/hr, as cold fluids are administered at higher flow rates there is a danger that the fluid will cause the patient's body temperature to fall, which may lead to cardiac dysfunctions or aggravate existing conditions such as shock or hypothermia. Thus, it is desirable to warm the fluid to a normal physiological temperature of approximately 37° C. prior to administration of the fluid to the patient.

In order to administer physiological fluids at acceptable infusion temperatures several devices have been proposed. U.S. Pat. Nos. 4,705,505 and 4,759,749 to Fried disclose an administration set including a heat exchanger to heat the fluid, in which the fluid is directed through multiple aluminum rods and water is directed around the outside of the rods to transfer heat to the fluid. As the fluid leaves the heat exchanger, its temperature is measured and it subsequently flows through 8 inches of tubing, a drip chamber, and an additional 18 inches of tubing prior to infusion into the patient. Thus, the fluid flows through over two feet of tubing in addition to a drip chamber after the temperature is monitored at the heat exchanger, during which time the fluid temperature may decrease an indeterminate amount as a result of heat transfer through the tubing and drip chamber to the surroundings.

In U.S. Pat. No. 4,759,749, issued to Verkaart, a heater for physiological fluids is disclosed in which a heat exchanger for the device is designed to be supported on a pole. The heat exchanger includes a central tube positioned within an outer tube, wherein a heating fluid is circulated through the central tube and the physiological fluid is heated as it flows along the outside of the central tube. After leaving the heat exchanger, the fluid flows through two additional lengths of tubing and a filter during which time its temperature may fall as it loses heat to the surroundings.

U.S. Pat. No. 4,531,941 to Zasuwa discloses a device for heating blood in which the blood is passed through multiple plastic capillary tubes while heated water is circulated around the tubes. The output temperature of the blood leaving this device does not match the input temperature of the warming fluid, in addition to varying with the input temperature of the blood, and thus makes it difficult to accurately control the blood temperature by means of a preset water temperature, which must typically be supplied at a temperature in excess of the desired output temperature for the physiological fluid. Further, additional tubing and a drip chamber is required between the heat exchanger device and the patient, which will result in the blood losing heat as it passes to the patient and further make the delivery temperature of the blood difficult to predict and control.

Finally, U.S. Pat. No. 3,881,483 issued to Sausse discloses a device for heating blood as it leaves a blood oxygenator. The heating device consists of an electrical heating element which is in direct contact with the blood carrying tube, which is an undesirable arrangement since it could potentially expose the patient to an electrical shock.

In general, physiological fluid heaters are limited by the temperature to which the fluid may be heated. For example, blood should not be heated to temperatures greater than 41° C. in order to avoid destruction of important components of the blood, such as red blood cells. Thus, there is a limit on the extent to which the temperature of the fluid in the warming device can be raised in order to compensate for any heat lost from the fluid after leaving the warmer and prior to reaching the patient.

There is a need for a physiological fluid warmer which provides high fluid flow rates of up to 160 ml/min while efficiently heating the fluid to a temperature of approximately 37° C. The warmer should also heat the fluid a minimal amount in order to avoid destruction of important fluid components, and provide a minimal distance from the warmer to the patient in order to minimize the heat lost from the fluid after it has been heated. In addition, the warmer should be configured to avoid exposing the patient to any potentially dangerous electrical heating elements.

SUMMARY OF THE INVENTION

The present invention is directed to a disposable physiological fluid warmer for warming fluids such as whole blood, packed red blood cells or plasma as it is administered to a patient. The warmer is constructed as a relatively small, compact unit which may be taped or otherwise supported on a patient's arm or at the end of an arm board attached to a patient's arm.

The fluid warmer is formed as a box within which is mounted a pair of connected coils for carrying a physiological fluid. The coils are separated by a partition which defines two elongated chambers and a passage between the chambers, such that a channel is formed to direct a warming fluid, such as water, to flow along the coils. The warm fluid flows through the chambers in a direction which is opposite to the flow of the physiological fluid through the coils.

In a preferred embodiment of the invention, the coils are formed from stainless steel tubing in order to provide good thermal conductivity and thus improve the rate of heat transfer between the warming fluid to the physiological fluid.

Also, in the preferred embodiment, a length of plastic tubing is connected to each of the coils, and a length of plastic tubing is connected in fluid communication with each of the chambers inside the box. The free end of the plastic tubing leading from an outlet end of the coil is provided with a male connector for connection to a venous entry device. The free end of the plastic tubing leading from an inlet end of the coil is provided with a female connector for connection to the outlet of a physiological fluid administration set. The free ends of the plastic tubing which are in fluid communication with the chambers are provided with connectors, which are color coded to indicate to the user the inlet and outlet tubes for the warming fluid.

The warmer may also be provided with tabs extending from opposite sides of the warmer by which the warmer may be taped, strapped or otherwise attached to a patient's arm or to an arm board attached to a patient's arm.

In addition, means are provided for monitoring the temperature of the physiological fluid and warming fluid and for controlling the operation of a heating element for heating the warming fluid.

Other objects and advantages of the present invention will be apparent from the following description, the accompanying drawings and the appended claims.

DETAILED DESCRIPTION OF THE PREFERRED EMBODIMENTS

Figure 1:
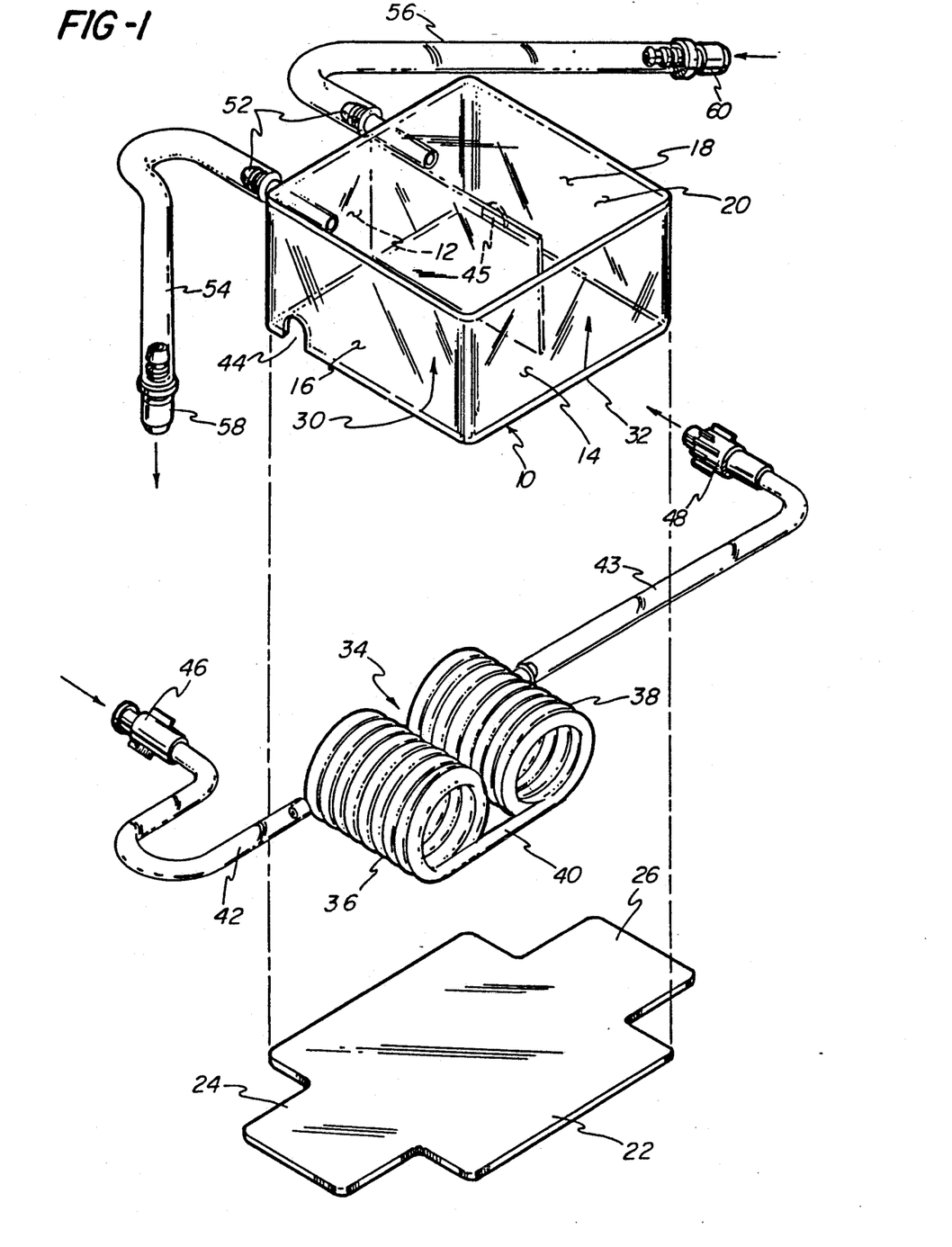
FIG. 1 is an exploded view of the fluid warmer.
Figure 2:
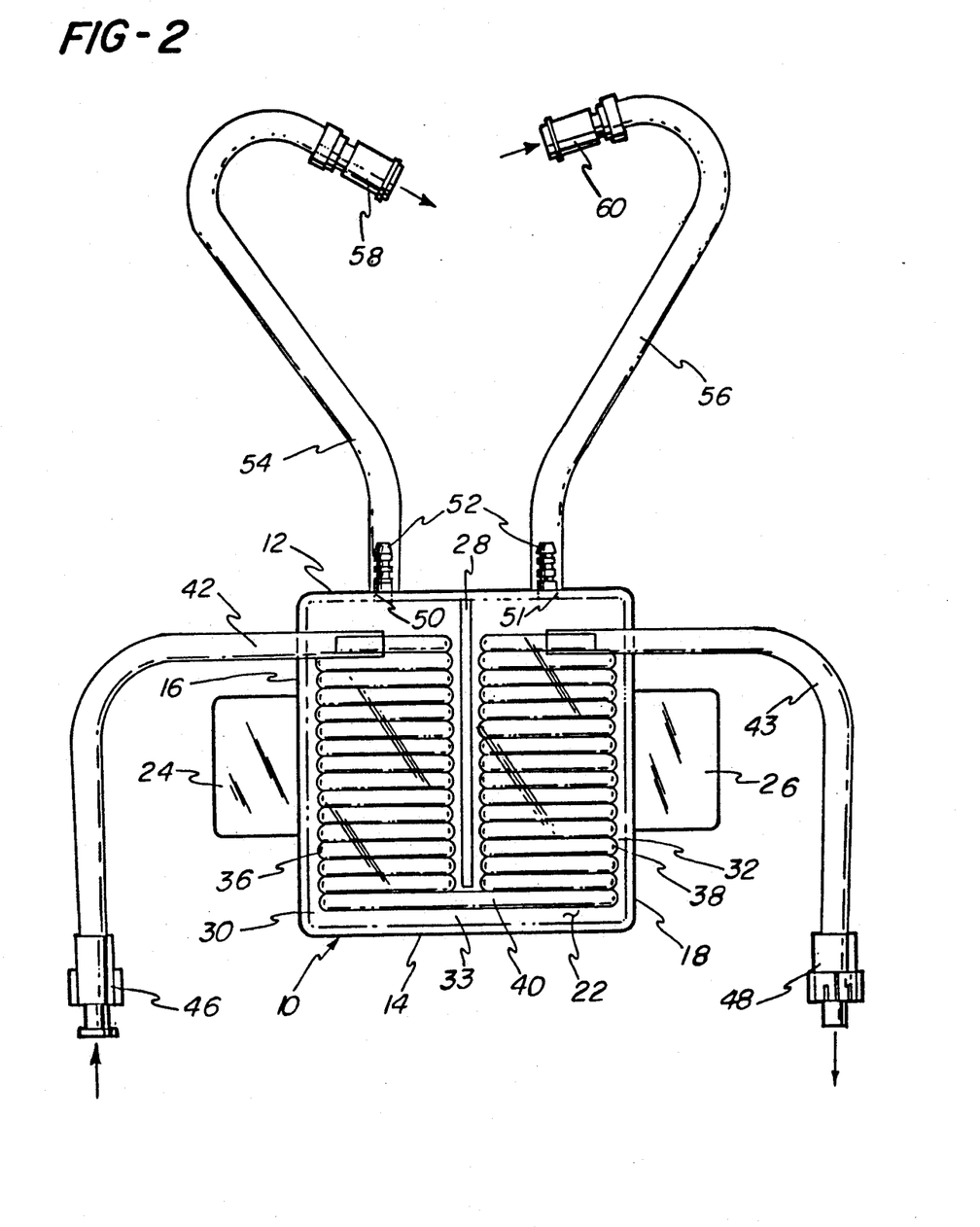
FIG. 2 is a top view of the fluid warmer with the top panel removed.

Referring to FIG. 1, the physiological fluid warmer includes a box 10 having a first side 12, an opposing second side 14, a third side 16, and an opposing fourth side 18. The sides are all of substantially equal length and are positioned perpendicular to a top portion 20 and a bottom portion 22 of the box 10. The bottom portion 22 may be provided with elongated substantially planar tabs 24, 26 extending out beyond the third and fourth sides 16,18 and parallel to the bottom portion. The sides are preferably formed with a maximum height of approximately 1 inch (2.54 cm), a maximum width of approximately 2 inches (5.08 cm) such that the box portion of the warmer occupies a maximum volume of approximately 4 in.$^3$ (65.5 cc). Thus, the box has a substantially square, compact configuration. In addition, the box is preferably formed from a transparent plastic material such as that sold under the trademark "LEXAN".

A partition 28 having a height equal to that of the sides is attached to an interior portion of the first side 12 and defines first and second elongated chambers 30, 32 within the box. The partition 28 extends from the first side toward the second side 14 and parallel to the third and fourth sides 16,18 to a point adjacent to, but spaced from, an interior portion of the second side 14, such that a passage 33 is defined between the first and second chambers 30, 32. The chambers 30, 32 and the passage 33 define a path for a warming fluid, such as water, to follow while flowing through the box.

A heat exchanger element 34 is positioned within the box 10 for conveying the physiological fluid through the warmer. The heat exchanger element 34 is constructed from a continuous length of stainless steel tubing, such as 304 stainless steel which has a thermal conductivity of approximately 46 J/s·m·° C., and is formed into first and second elongated helical coils 36, 38 wherein each of the coils is formed by a plurality of turns of the tubing. The turns of the tubing defining the coils 36, 38 each define a central axis of a respective coil.

The first and second coils 36, 38 are positioned in the first and second chambers 30,32, respectively, such that the central axes of the coils 36, 38 are aligned substantially parallel to each other, and the coils are connected by a length of straight tubing 40 which extends through the passage 33 between the chambers. The tubing used in the heat exchanger element 34 is selected to have the same interior diameter as that of the tubing used in a standard administration set, which is typically about 0.254 cm, with a wall thickness of approximately 0.030 cm and a length of about 190 cm.

In the preferred embodiment, the tubing forming the heat exchanger element 34 hats an interior surface of a predetermined circumference which defines a continuous, fluid-tight passage therethrough out of fluid contact with the interior of the box 10, and an exterior surface in heat transfer relationship with a warming fluid conveyed through the chambers 30, 32. The tubing is further formed having a substantially uniform inner circumference along the length of the tubing from an inlet end to an outlet end thereof in order to maintain a smooth flow path for the physiological fluid whereby the formation of air bubbles and fluid stagnation points within the heat exchanger element 34 is avoided. The inner circumference of the tubing is preferably approximately 0.80 cm.

The provision of stainless steel tubing for the heat exchanger element 34 represents an improvement over other materials used to convey physiological fluids through warmers, in that stainless steel is an easily sterilized material and also provides an efficient heat transfer medium with a high degree of thermal conductivity between the physiological fluid and the warming fluid. As a result of using a material with a high thermal conductivity, a shorter length of tubing for the coils 36, 38 is required in order to achieve the desired degree of heat transfer, resulting in a much more compact unit, and thus less priming volume. For example, the priming volume of the present embodiment is approximately 7 cc.

First and second lengths of flexible plastic tubing 42, 43 formed with an inner circumference approximately equal to that of the heat exchanger element tubing are connected to the first and second coils 36, 38, respectively, and pass through apertures 44, 45 defined in the third and fourth walls 16, 18 adjacent to the first wall 12 and to the bottom portion 22. The free end of the first length of tubing is provided with a female connector 46 to be connected to the outlet end of a physiological fluid administration set, and the free end of the second length of tubing is provided with a male connector 48 to be connected directly to a venous entry device such as a hypodermic needle. The male and female connectors 46,48 may be of the type sold under the name "LUER-LOK". The connectors on the ends of the tubing clearly indicate to the user the appropriate tubes for input and output of the physiological fluid.

In addition, the second length of flexible plastic tubing 43 is provided as a short length of tubing such that the heat lost by the physiological fluid after it leaves the warmer is minimized. Preferably, the second length of tubing 43 is less than one foot, as measured from the warmer to the male connector 48, such that only enough tubing is provided to allow the warmer to be mounted on a surface directly adjacent to the entry point for the physiological fluid.

First and second openings 50, 51 are defined in the first wall 12 of the box 10 for passage of a warming fluid into the chambers 30, 32. The first opening is located between the third wall 16 and the partition 28 and the second opening is located between the fourth wall 18 and the partition 28 such that each of the chambers 30, 32 is provided with an opening for the warming fluid.

Barbed connectors 52 are located on the first wall 12 at each of the openings 50, 51 to provide means for attaching third and fourth lengths of flexible plastic tubing 54, 56 in fluid communication with the chambers 30, 32. Color coded connectors 58, 60 are attached to the free ends of the third and fourth lengths of tubing 54, 56. The connectors may be of the type sold as "snap lock" connectors. The colors on the connectors 58, 60 are selected so as to indicate to the user the proper connections for warming fluid inlet and outlet. For example, the inlet connector 60 may be colored red to indicate warm fluid entering the warmer, and the outlet connector 58 may be colored blue to indicate cooled fluid leaving the warmer.

The direction of flow selected for the physiological fluid, as indicated by the connectors 46, 48, is in the direction opposite from the direction of flow of the warming fluid, as indicated by the colors of the connectors 58, 60. In other words, as the physiological fluid is flowing from the first coil 36 in the first chamber 30 to the second coil 38 in the second chamber 32, the warming fluid is flowing in the opposite direction into the second chamber 32, along the length of the second coil 38, through the passage 33 between the chambers, along the length of the first coil 36, and out of the first chamber 30. In this manner, an optimum temperature differential is maintained across the two fluid flows at all locations through the warmer, and the resulting heat transfer between the fluids is maximized.

Figure 3:
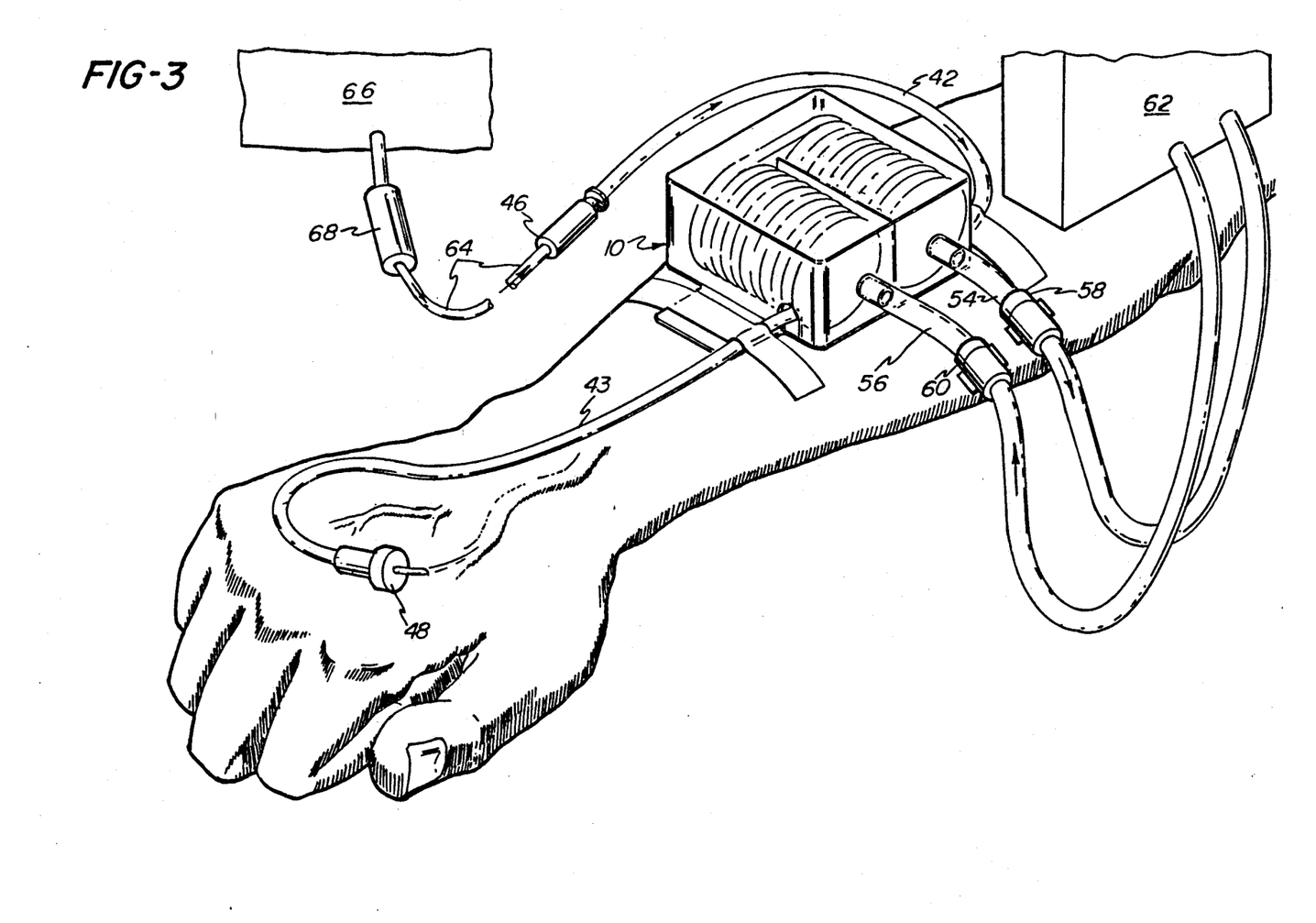
FIG. 3 shows the fluid warmer in use attached to a patient's arm.

The operation of the physiological fluid warmer is as follows. The connectors 58, 60 are connected to the output and input sides of a source of warming fluid 62, such as a water heater, which preferably supplies water at a temperature of 38° C. and a flow rate of approximately 56 liters/hr. The air is primed out of the warmer box by rotating the box 10 to move any air bubbles toward the first opening in the first chamber 30, from which they will pass out of the box. This operation is facilitated by the transparent sides of the box 10 which allow the user to see the air bubbles within the box 10.

The female connector 46 may then be connected to the output of a physiological fluid administration set 64 which conveys fluid from a physiological fluid supply 66 and a drip chamber 68. The air may then be primed out of the physiological fluid system, including the warmer, after which the male connector 48 is connected to a venous entry device for infusion of the fluid to the patient. It should be noted that the tubing of the heat exchanger element 34 is easily primed with the administration set 64 since both consist of the same diameter tubing, and thus points along the fluid path at which air may become trapped are avoided.

If the venous entry device is located at the patient's hand, the warmer is preferably attached to the top of the patient's forearm near the entry device or, alternatively, the warmer may be attached to the end of an arm board on a patient's arm. The warmer may be attached by means of tape which passes over the top of the tabs 24, 26 and adhere to the patient's arm, however, elastic or VELCRO straps may also be used to attach the warmer. In addition, since the first and second tubes 42, 43 are adjacent to the bottom portion 22 of the warmer, they may be attached to the patient's arm to hold them in place at the same time as the tabs 24, 26 are taped in place.

The present invention, as described above, is capable of efficiently warming a physiological fluid from an initial temperature of 4° C. to a normal body temperature of 37° C. at fluid flow rates of up to 160 ml/min when a warming fluid is supplied at a temperature of 38° C. Further, if lower fluid flow rates are used, the highest temperature to which the fluid will be heated will be that of the water, and since the heat loss from the fluid as it travels between the warmer and the entry device is minimized, there is no need to heat the fluid above normal physiological temperature. Thus, there is no danger that the fluid will be heated to a temperature which will result in destruction of important fluid components, such as red blood cells.

While the above-described device comprises a preferred embodiment of the present invention when warming physiological fluids to the temperatures and at the flow rates described above, it has been found that there is a need for effectively warming physiological fluids at higher flow rates. In particular, there is a need for a device to warm fluids at flow rates as high as 210 ml/min.

In accordance with this need, the above-described fluid warmer has been modified such that it is formed with a maximum height of approximately 1.25 inches (3.18 cm), a maximum width of approximately 2.5 inches (6.35 cm) and a maximum length of approximately 2.5 inches (6.35 cm) such that the warmer occupies a maximum volume of approximately 7.81 in.$^3$ (128.1 cc).

In addition, the stainless steel tube forming the coils has a slightly larger internal diameter of approximately 0.30 cm and a length of approximately 238 cm such that the priming volume of the present embodiment is approximately 11 ml. Further, the wall thickness of the tubing is approximately 0.035 cm such that the heat transfer characteristics of the present embodiment are substantially similar to those of the previous embodiment. However, due to the increased surface area of the coils, the physiological fluid may be warmed at a higher rate than the previous embodiment and thus may be allowed to pass through the warmer at a higher flow rate.

It should be noted that physiological fluid administration sets are typically provided with a means for increasing the pressure of the physiological fluid as it passes from the fluid source to the venous entry device. Such pumping devices usually supply the physiological fluid at a maximum pressure of 30 mm of mercury. However, the physiological fluid is typically delivered at lower pressures, and the fluid warmer of the present embodiment is designed to operate at pressures of approximately 25 mm of mercury, although it is capable of handling the maximum pressure which the pump can supply.

Further, the fluid warmer of the present invention will also operate efficiently at lower flow rates such as those required to provide intravenous flows for neonatal patients. The flow rate in such an application may be as low as 10 ml per minute or as high as 15 ml per minute, depending upon the particular need.

It should be apparent that the present embodiment provides a compact fluid warming device which may be attached to a patient. Further, the present fluid warmer is an improvement over the prior art devices in that the fluid path for the physiological fluid does not require the fluid to undergo any sharp changes in direction and does not include any large diameter changes in the fluid path, such that problems associated with the formation of bubbles at such changes in direction and variations in flow path diameter are avoided.

Some typical experimental results which have been produced by the fluid warmer of the present embodiment are as follows:

| Blood Flow Rate | Blood Temp. In | Blood Temp. Out | Water Temp. | Water Flow Rate |
| --- | --- | --- | --- | --- |
| 80 ml/min | 4° C. | 37.1° C. | 38° C. | 94.7 liters/hour |
| 100 ml/min | 10° C. | 36.8° C. | 38° C. | 94.7 liters/hour |
| 160 ml/min | 4° C. | 36.8° C. | 39.5° C. | 94.7 liters/hour |
| 160 ml/min | 10° C. | 36.9° C. | 39.0° C. | 94.7 liters/hour |
| 195 ml/min | 10° C. | 36.5° C. | 40.0° C. | 94.7 liters/hour |
| 210 ml/min | 10° C. | 36.1° C. | 40.0° C. | 94.7 liters/hour |

With regard to the above results, it should be noted that the temperature of the water or warming fluid supplied to the fluid warmer will typically drop less than 0.5° C. while passing through the warmer.

Figure 4:
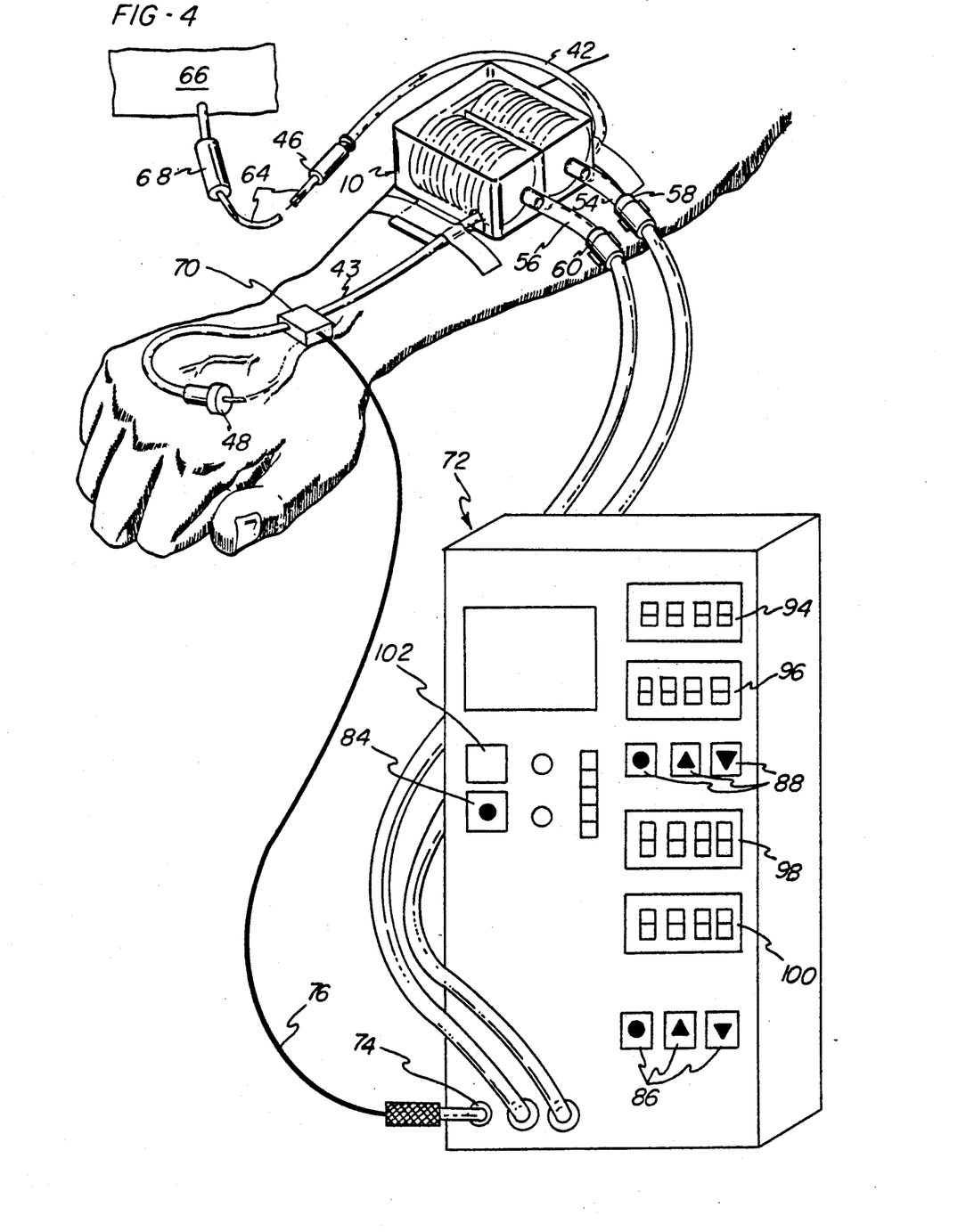
FIG. 4 shows a second embodiment of the fluid warmer in use attached to a patient's arm.
Figure 5:
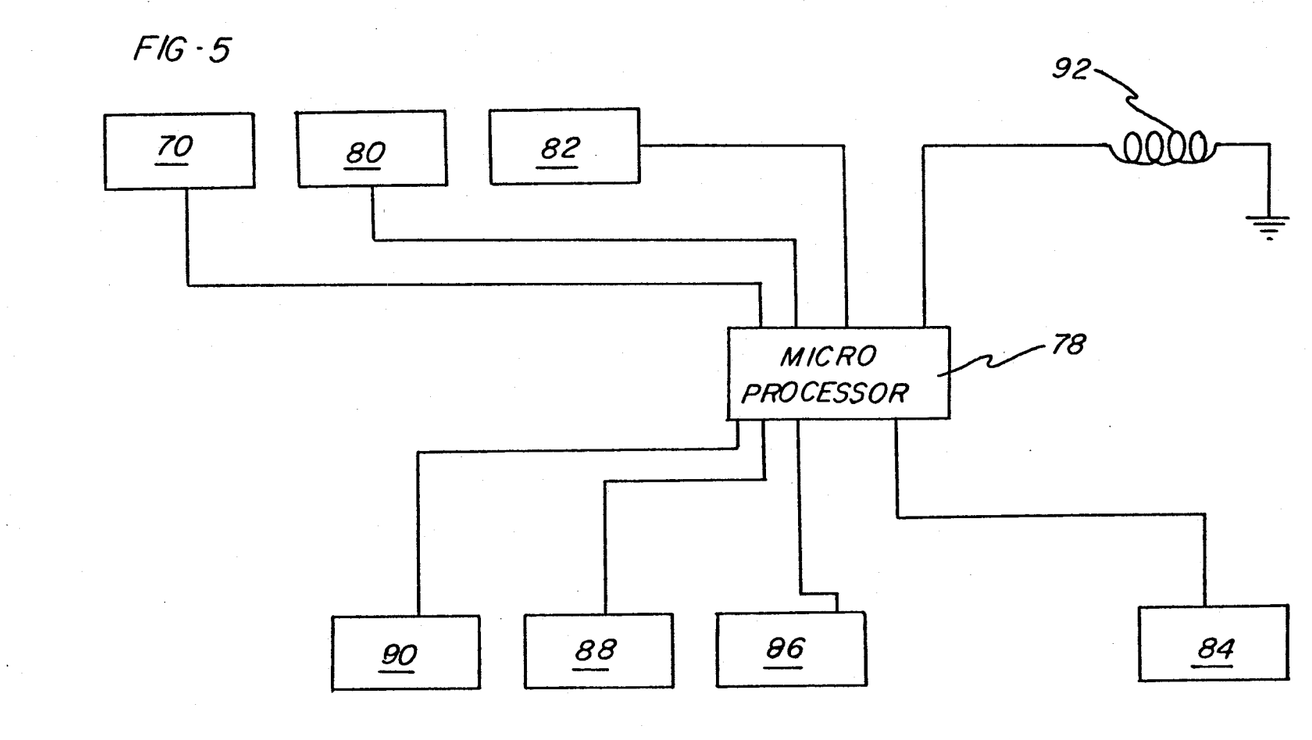
FIG. 5 is a diagram of sensing and control components to control the warming fluid temperature in accordance with the embodiment of FIG. 4.

Referring to FIGS. 4 and 5, a further embodiment of the present invention is illustrated and will be described with reference to blood as the physiological fluid, although other fluids may be used. As may be seen in FIG. 4, a temperature sensor 70 is located in the blood path defined by the tube 43 between the fluid warmer box 10 and the venous entry device attached to the connector 48.

A temperature adjustable source of warming fluid 72 is provided and includes an outlet 74 for receiving one end of an insulated sensing wire 76 extending from the blood temperature sensor 70. The outlet 74 is electrically connected to a microprocessor contained within the unit 72 for controlling the temperature of the warming fluid.

As is shown diagrammatically in FIG. 5, the microprocessor 78 receives the outputs from the blood temperature sensor 70 as well as a water temperature sensor 80 and a water over temperature switch circuit 82. In addition, the microprocessor 78 is connected to a series of switches including a start switch 84 for starting the operation of the warmer, switches 86 for setting the warmer to operate at a desired blood temperature, as sensed by the sensor 70, switches 88 for setting the warmer to operate at a desired water temperature as sensed by sensor 80, and a switch 90 to select a mode of operation for the warmer to operate in response to either the desired water temperature or desired blood temperature.

In addition, the unit 72 shown in FIG. 4 may include displays 94, 96, 98, 100 for displaying the measured water temperature, the water temperature set point, the measured blood temperature and the blood temperature set point, respectively. Also, a switch 102 may be provided for selecting whether the display is given in Fahrenheit or Centigrade.

The water sensor 80 and over temperature switch circuit 82 are located adjacent to each other within the unit 72 for sensing the warming fluid temperature as it returns from the physiological fluid warmer. The microprocessor 78 preferably controls power to an electrical heater element 92 within the unit 72 to thereby control the temperature of the warming fluid. The microprocessor 78 is programmed such that it will operate in response to either the output of the blood temperature sensor 70 or the output of the water temperature sensor 80 in separate modes of operation. The particular sensor which the microprocessor 78 refers to in controlling the heater element may be selected by the mode select switch 90.

Thus, if the blood temperature sensor mode is selected, the microprocessor 78 will refer to the desired blood temperature as set by the set switches 86, and compare the output of the sensor 70 to this desired temperature as it controls power to the heater element 92. Alternatively, if the water temperature mode is selected, the microprocessor 78 will refer to the desired water temperature, as set by the switches 88, as it receives a temperature signal from the water temperature sensor 80.

As noted above, a water over temperature switch circuit 82 is also provided and operates to prevent the warming fluid from being heated to an excessive temperature if either of the sensors 70 or 80 should fail. The sensor 82 is located in the warming fluid return line adjacent to the sensor 80 and includes a thermostat controlled switch which signals the microprocessor 78 to shut off the heater element when the thermostat in the switch circuit 82 reaches a predetermined fluid temperature. In the preferred embodiment, the predetermined temperature is 41° C.

It should be noted that the water over temperature switch circuit 82 operates in both the blood temperature sensor mode and the water temperature sensor mode such that the physiological fluid is prevented from being overheated during any mode of operation of the fluid warming unit 72.

While the forms of apparatus herein described constitute preferred embodiments of the invention, it is to be understood that the invention is not limited to these precise forms of apparatus and that changes may be made therein without departing from the scope of the invention which is defined in the appended claims:

What is claimed is:

1. In combination with a source of a physiological fluid, a venous entry device for infusion of said physiological fluid into a patient at an infusion site, and a source of heat transfer fluid maintained at a preselected temperature, the improvement comprising:

a chamber having an exterior surface adapted to be attached to and supported by said patient such that said chamber may rest upon a skin surface of said patient at said infusion site, means defining a fluid-tight interior in said chamber including walls defining an exterior surface of said chamber, means for conveying said heat transfer fluid from and to said source thereof to and from, respectively, said interior of said chamber, a continuous single length of tubing positioned within said interior of said chamber, said tubing having an interior surface defining a continuous, fluid-tight passage therethrough out of fluid contact with said interior of said chamber and an exterior surface in heat transfer relationship with a heat transfer fluid conveyed through said interior of said chamber, said tubing further including opposing ends wherein one of said ends of said tubing defines an upstream end located adjacent to one of said walls to define an entry point for said physiological fluid through one of said chamber walls and into said tube and wherein the other of said ends defines a downstream end located adjacent to one of said walls to define an exit point for said physiological fluid through one of said chamber walls and out of said tube, means for conveying said physiological fluid from said source thereof to said upstream end of said tubing for flow through said passage, means for conveying said physiological fluid from said downstream end of said tubing to said venous entry device wherein said means for conveying physiological fluid to and from said tubing define continuous fluid-tight passages passing through said chamber walls and connected to respective ends of said single length of tubing, and said means for conveying said physiological fluid from said downstream end of said tubing having a length of less than one foot from said downstream end of said tubing to said venous entry device, such that the heat lost by said physiological fluid after leaving said chamber is minimized.

2. The combination of claim 1 wherein said tubing is formed of stainless steel.

3. The combination of claim 2 wherein said tubing comprises coils.

4. The combination of claim 3 wherein said tubing comprises two coils.

5. The combination of claim 4 wherein said tubing is formed of a material having a thermal conductivity of approximately 46 J/s·m·°C.

6. The combination of claim 5 wherein said tubing has a wall with a thickness of approximately 0.030 cm.

7. The combination of claim 1 wherein the length of said tubing is about 190 cm.

8. The combination of claim 7 wherein said tubing has a priming volume of approximately 7 cc.

9. The combination of claim 8 wherein said chamber has a maximum width and a maximum height dimension, said maximum width dimension not exceeding 2 inches and said maximum height dimension not exceeding 1 inch.

10. The combination of claim 1 wherein said continuous length of tubing comprises first and second elongated coils and each elongated coil is defined by a plurality of turns of said tubing.

11. The combination of claim 10 wherein the first and second elongated coils are positioned parallel to one another.

12. The device of claim 11 wherein means are provided for dividing said chamber into first and second portions for receiving said first and second coils and means are provided for defining a passage between said first and second portions.

13. The device of claim 12 wherein a single length of said tubing extends through said means for connecting said first and second coils.

14. The device of claim 13 wherein said chamber comprises a top and a bottom portion, a first side, a second side opposite to said first side, a third side, and a fourth side opposite to said third side, and said top and bottom portions being positioned substantially perpendicular to said sides.

15. The device of claim 14 herein said bottom portion is provided with tabs extending out beyond said third and fourth sides and substantially parallel to said bottom portion such that said tabs may be taped to a surface for supporting said device.

16. The device of claim 14 wherein said means dividing said chamber into said first and second portions is a partition extending from said top portion to said bottom portion, said partition being attached to an interior portion of said first side and extending substantially parallel to and substantially midway between said third and fourth sides, said partition extending from said interior portion of said first side to a point adjacent to and spaced from an interior portion of said second side to define said passage between said first and second portions.

17. The device of claim 16 wherein said means for conveying said physiological fluid to said tubing passes through said third side adjacent to said first side and to said bottom portion, and said means for conveying said physiological fluid from said tubing passes through said fourth side adjacent to said first side and to said bottom portion.

18. The device of claim 17 wherein said means for conveying said heat transfer fluid to said interior of said chamber passes through said first wall between said partition and said fourth side, and said means for conveying said heat transfer fluid from said interior of said chamber passes through said first wall between said partition and said third side, such that said heat transfer fluid may flow along the length of said second portion, through said passage, and along the length of said first portion before passing out of said chamber, while the physiological fluid may flow through said first coil in said first portion and then through said second coil positioned in said second portion, such that said physiological fluid flows counter to the flow of said heat transfer fluid, whereby heat transfer between said heat transfer fluid and said physiological fluid is maximized.

19. The device of claim 18 wherein said coil tubing is formed of stainless steel to further maximize the heat transfer within said chamber.

20. The device of claim 19 wherein said means for conveying said physiological fluid and said heat transfer fluid comprise flexible plastic tube.

21. A fluid warmer in combination with a source of physiological fluid, a venous entry device for infusion of said physiological fluid into an infusion site on a patient, and a source of heat transfer fluid, said fluid warmer comprising:

a chamber including walls defining an exterior and a fluid-tight interior, said chamber having a maximum volume of approximately 128.1 cc whereby said chamber is adapted to be attached to and supported by said patient with said chamber exterior positioned in contact with and supported by a skin surface of said patient, means for conveying said heat transfer fluid from and to said source thereof to and from, respectively, said interior of said chamber, a continuous single length of tubing positioned within said interior of said chamber, said tubing having an interior surface of a predetermined inner circumference defining a continuous, fluid-tight passage therethrough out of fluid contact with said interior of said chamber and an exterior surface in heat transfer relationship with a heat transfer fluid conveyed through said interior of said chamber, and said tubing having opposing ends, one of said ends defining an upstream end located adjacent to means defining an opening through one of said walls to define an entry point for said physiological fluid into said tubing, the other of said ends defining a downstream end located adjacent to means defining an opening through one of said walls to define an exit point for said physiological fluid out of said tubing, means attached to said tubing for conveying said physiological fluid from said source thereof to said upstream end of said tubing for flow through said passage, means attached to said tubing for conveying said physiological fluid from said downstream end of said tubing to said venous entry device, and wherein all of said physiological fluid conveyed into and out of said chamber passes through said continuous single length of tubing, and said predetermined inner circumference is such that said physiological fluid may pass through said tubing at a flow rate of at least 10 ml/min when a maximum fluid pressure of 30 mm of Hg is applied to said physiological fluid between said source thereof and said chamber.

22. The fluid warmer of claim 21 wherein said means for conveying said physiological fluid from said downstream end of said tubing has a length of less than one foot from said downstream end of said tubing to said venous entry device, such that the heat lost by said physiological fluid after leaving said chamber is minimized.

23. The fluid warmer of claim 21 including first sensing means located within said means for conveying said physiological fluid from said downstream end of said tubing for sensing the temperature of said physiological fluid after exiting the temperature of said physiological fluid after exiting said fluid warmer and control means for receiving an input from said sensing means.

24. The fluid warmer of claim 23 including second sensing means for sensing the temperature of said heat transfer fluid as it returns to said source of heat transfer fluid and for providing an input to said control means.

25. The fluid warmer of claim 24 wherein said source of heat transfer fluid includes a heater element controlled by said control means in response to inputs from said first and second sensing means for heating said heat transfer fluid.

26. The fluid warmer of claim 25 wherein said control means includes means for selecting a desired reference temperature for said physiological fluid at said first sensing means and means for selecting a desired reference temperature for said heat transfer fluid at said second sensing means, and means for selecting a mode of operation whereby said control means controls said hater element either with reference to said physiological fluid reference temperature and inputs from said first sensing means or with reference to said heat transfer fluid reference temperature and inputs from said second sensing means.

27. The fluid warmer of claim 26 including third sensing means for sensing the temperature of said heat transfer fluid and causing said control means to shut off said heater element upon sensing a predetermined maximum temperature.

28. The fluid warmer of claim 27 wherein said third sensing means is located adjacent to said second sensing means.

29. The fluid warmer of claim 25 including third sensing means for sensing the temperature of said heat transfer fluid and causing said controller to shut off said heater element upon sensing a predetermined maximum temperature.

30. The fluid warmer of claim 21 wherein said chamber has a maximum height of approximately 3.18 cm, a maximum width of approximately 6.35 cm and a maximum length of approximately 6.35 cm.

31. The fluid warmer of claim 21 wherein said predetermined inner circumference is substantially uniform along the length of said tubing from said entry point to said exit point of said chamber and said predetermined circumference is at least approximately 0.80 cm.

32. The fluid warmer of claim 21 wherein said chamber walls include a first wall and a second wall in opposing relation to said first wall, a partition extending from a point in contact with said first wall to a point spaced from said second wall to define first and second portions within said chamber and a connecting passage between said partition and said second wall whereby said warming fluid may flow from said first to said second portion, said tubing extending through said first and second portions and said connecting passage.

33. The fluid warmer of claim 21 wherein said tubing is in the shape of a first elongated helical coil formed by a plurality of turns of said tubing defining a central axis of said coil and means are provided for directing said warming fluid through said chamber in a direction substantially parallel to said central axis.

34. The fluid warmer of claim 33 including a second elongated helical coil formed by a plurality of turns of said tubing defining a central axis of said second coil substantially parallel to said central axis of said first coil.

35. The fluid warmer of claim 21 including at least one elongated substantially planar tab member extending away from said chamber such that said at least tab member may be taped to a surface for supporting said fluid warmer.

36. The fluid warmer of claim 21 wherein said chamber includes two opposing walls and said entry point is located in one of said opposing walls and said exit point is located in the other of said opposing walls.

37. The fluid warmer of claim 21 wherein in said means for conveying said physiological fluid to and from said tubing has an inner circumference substantially equal to said predetermined circumference of said inner surface of said tubing.

* * * * *

UNITED STATES PATENT AND TRADEMARK OFFICE
CERTIFICATE OF CORRECTION

PATENT NO. : 5,254,094
DATED : 10/19/93
INVENTOR(S) : David Lynn Starkey et al

It is certified that error appears in the above-identified patent and that said Letters Patent is hereby corrected as shown below:

Column 9, line 56, "said means" should be --said passage means--.
Column 11, lines 34 and 35, "the temmperature of said physiological fluid after exiting" should be deleted; line 53, "hater" should be --heater--.

Signed and Sealed this

Twenty-ninth Day of March, 1994

Attest:

BRUCE LEHMAN

*Attesting Officer*   *Commissioner of Patents and Trademarks*